United States Patent
Rothgeb et al.

(10) Patent No.: US 6,958,693 B2
(45) Date of Patent: Oct. 25, 2005

(54) SENSOR DEVICE AND METHODS FOR USING SAME

(75) Inventors: Timothy Michael Rothgeb, Cincinnati, OH (US); Kristina Marie Rohal Gansle, Cincinnati, OH (US); Jonathan Livingston Joyce, Independence, KY (US); James Madison Jordan, Hamilton, OH (US); Tedd Addison Rohwer, Albuquerque, NM (US); Randal Ray Lockhart, Albuquerque, NM (US); Christopher Lawrence Smith, Liberty Township, OH (US); Toan Trinh, Maineville, OH (US); Mark Gary Cipollone, New Richmond, OH (US)

(73) Assignees: Procter & Gamble Company, Cincinnati, OH (US); Sandia Corporation, Albuquerque, NM (US)

( * ) Notice: Subject to any disclaimer, the term of this patent is extended or adjusted under 35 U.S.C. 154(b) by 122 days.

(21) Appl. No.: 10/441,595

(22) Filed: May 20, 2003

(65) Prior Publication Data

US 2003/0227394 A1 Dec. 11, 2003

Related U.S. Application Data

(60) Provisional application No. 60/383,012, filed on May 24, 2002.

(51) Int. Cl.[7] .......................... G08B 1/08; G08C 19/16; B08B 13/00
(52) U.S. Cl. .............................. 340/539.22; 340/539.1; 340/522; 340/539.26; 340/870.01; 340/618; 134/113; 222/23
(58) Field of Search ................... 340/539.1, 539.26, 340/539.11, 539.22, 693.5, 691.1, 540, 321, 340/546, 618–623, 870.01; 702/30, 188; 222/23, 52; 134/113, 56 R, 56 D, 57 R, 57 D

(56) References Cited

U.S. PATENT DOCUMENTS

| | | | |
|---|---|---|---|
| 3,645,669 A | 2/1972 | Rausch | 68/12.18 |
| 3,875,424 A | 4/1975 | Hopkins | 307/117 |
| 4,025,912 A | 5/1977 | Rice | 340/870.17 |
| 4,590,466 A | 5/1986 | Wiklund et al. | 340/870.28 |
| 4,718,776 A | 1/1988 | Giland et al. | 374/170 |
| 5,132,968 A * | 7/1992 | Cephus | 370/349 |
| 5,253,379 A | 10/1993 | Dusamos et al. | 137/5 |
| 5,283,549 A * | 2/1994 | Mehaffey et al. | 340/521 |
| 5,404,606 A | 4/1995 | Mueller | 68/12.02 |
| 5,532,679 A * | 7/1996 | Baxter, Jr. | 340/539.26 |
| 5,650,770 A * | 7/1997 | Schlager et al. | 340/573.1 |
| 5,682,774 A | 11/1997 | Baumgardner | 68/235 R |
| 5,892,690 A * | 4/1999 | Boatman et al. | 700/276 |
| 6,057,773 A * | 5/2000 | Shukla et al. | 340/623 |
| 6,317,029 B1 * | 11/2001 | Fleeter | 340/10.32 |
| 6,452,499 B1 * | 9/2002 | Runge et al. | 340/601 |
| 6,536,060 B1 | 3/2003 | Janssens et al. | 134/113 |
| 2002/0078979 A1 | 6/2002 | Aulbers et al. | |

FOREIGN PATENT DOCUMENTS

DE  40 31 981 A1  4/1992

(Continued)

*Primary Examiner*—Donnie L. Crosland
(74) *Attorney, Agent, or Firm*—C. Brant Cook; Caroline Wei-Berk; Kim W. Zerby

(57) ABSTRACT

A sensor device and method of employment is provided. More specifically, a sensor device adapted to detect, identify and/or measure a chemical and/or physical characteristic upon placement of the device into an environment, especially a liquid medium for which monitoring is sought is provided.

19 Claims, 3 Drawing Sheets

FOREIGN PATENT DOCUMENTS

| | | |
|---|---|---|
| EP | 0 178 031 | 4/1986 |
| EP | 0 210 509 | 4/1987 |
| EP | 0 237 088 B1 | 9/1987 |
| EP | 0 506 137 A1 | 9/1992 |
| EP | 0 580 643 B1 | 2/1994 |
| EP | 0 633 342 B1 | 1/1995 |
| EP | 0 644 291 A1 | 3/1995 |
| EP | 0 726 978 B1 | 8/1996 |
| EP | 0 748 892 B1 | 12/1996 |
| EP | 1 088 927 A1 | 4/2001 |
| EP | 1 281 446 A1 | 5/2003 |
| GB | 2 217 050 A | 10/1989 |
| WO | WO 92/18680 | 10/1992 |
| WO | WO 95/12704 | 5/1995 |
| WO | WO 95/22648 | 8/1995 |
| WO | WO 97/09480 | 3/1997 |
| WO | WO 98/35088 | 8/1998 |
| WO | WO 00/09997 | 2/2000 |
| WO | WO 01/07702 A1 | 2/2001 |
| WO | WO 01/70422 A1 | 9/2001 |
| WO | WO 02/29150 A1 | 4/2002 |
| WO | WO 03/018897 | 3/2003 |

* cited by examiner

SENSOR DEVICE AND METHODS FOR USING SAME

CROSS REFERENCE TO RELATED APPLICATION

This application claims the benefit of U.S. Provisional Application No. 60/383,012, filed May 24, 2002.

This invention was made with Government support under Contract No. DE-AC04-94AL85000 awarded by the Department of Energy. The Government has certain rights in the invention.

FIELD OF THE INVENTION

The present invention relates to a sensor device and method of employment. More specifically, the present invention relates to a sensor device adapted to detect, identify and/or measure a chemical and/or physical characteristic of an environment upon placement of the device into the environment, especially a liquid medium for which monitoring is sought. The present invention further relates to a method of doing business that involves the remittance of the sensor device to an environment to detect, identify and/or measure a chemical and/or physical characteristic of the environment which preferably is a characteristic that can be adjusted, e.g., in order to ameliorate the environment and/or to achieve and/or improve the end results that the environment is designed to provide.

The present invention is particularly useful in monitoring the environments in which fabric articles and/or dishes are cleaned and/or conditioned, yet is also useful in monitoring other environments. Thus, embodiments of the present invention particularly relate to methods of doing consumer research with respect to the cleaning of laundry and/or dishes, especially in automatic washing machines and/or dishwashing machines utilizing the sensor device, especially for determining consumer habits and practices. The invention also relates to methods for doing laundry and/or dishes in automatic machines, including both individual consumer and commercial operations and including "dry cleaning" operations and to methods of doing business in which the sensor device is utilized.

BACKGROUND OF THE INVENTION

The detergency art continues to evolve, particularly with the advent of new types of fabric, and consequently, new types of fabric cleaning and/or conditioning products. The detergency art has experienced similar expansion in the area of dishwashing, whether automatic or manual. Indeed, there exists a plethora of fabric and dish cleaning and/or conditioning products in the marketplace, each of which purports to achieve a different objective. Those skilled in detergency art have generally relied on the duplication of typical fabric and dish cleaning and/or conditioning environments in which to develop and analyze new fabric and dish cleaning and/or conditioning products. The duplication of these environments has certainly proven to be useful, as evidenced by the successful development of many, new fabric and dish cleaning and/or conditioning products. Nevertheless, the duplication of cleaning and/or conditioning environments is dependent upon the accurate identification and replication of the typical manners in which consumers clean and/or condition their fabric articles and dishes. Consumers oftentimes have difficulty in keeping accurate and complete records of their habits and practices. As a result, those skilled in the detergency art must often conduct surveys and lengthy investigations to ascertain the mode in which consumers typically employ fabric and dish cleaning and/or conditioning products.

In an effort to more accurately identify the properties of the environments in which consumers tend to clean and/or condition fabric and dishes, those skilled in the art have sought to develop monitoring devices that may be placed directly into a fabric and dish cleaning and/or conditioning environment, including that of a consumer and/or a laboratory testing facility. Skilled artisans have rigorously attempted to resolve this dilemma, as evidenced by the development of a few such devices in the recent past. Unfortunately, the development of these devices has had the general affect of complicating, rather than simplifying, the efforts to monitor particular environments. These complications are due largely in part to the fact that current monitoring devices are capable of measuring only one chemical and/or physical parameter. Thus, in order to measure several, chemical and/or physical parameters, practitioners must deploy a multitude of devices.

One prior art attempt at a monitoring device is described in PCT Publication No. WO 01/07702. The monitoring device described and illustrated in this reference is not without shortcomings. The device is described and illustrated as requiring a "sample reservoir" in which an aliquot of a wash fluid is captured and measured. The device is designed such that the capturing of an aliquot into the sample reservoir is easier than the evacuation of such aliquot from the sample reservoir due to the "funnel-shaped channel" which leads to the sample reservoir. As a result of this sample reservoir, this device can only measure parameters when, and if, a sample of wash liquid is present in the sample reservoir. Thus, this device is not capable of providing "real-time" measurement of parameters within the wash fluid because there is a delay between getting fluid into the sample reservoir and measuring the parameters once the fluid is present in the reservoir. In other words, the measuring means of this device are not in constant contact with the entire volume of the liquid continuously, but rather just a time-specific sample thereof. Further, once a sample is present in the sample reservoir, it is difficult, if not impossible, to remove all of the measured sample to ensure that the reservoir is clean before a next sample to be measured enters the reservoir. In light of the foregoing, it is clear that this prior art device is not capable of providing accurate measurements of a fluid, which is in a state of flux with regard to its conditions.

Accordingly, there is a need for a sensor device that is capable of continuously detecting, identifying and/or measuring a chemical and/or physical characteristic of an environment, especially a liquid medium, and most especially in the research into, and operation of, automatic laundering and dishwashing machines, especially under real life conditions.

SUMMARY OF THE INVENTION

The present invention addresses and solves all of the problems associated with deployment of conventional monitoring devices. The sensor device of the present invention facilitates the monitoring of chemical and/or physical characteristics in virtually any environment, particularly any gaseous and/or liquid environment, particularly a fabric and/or dish cleaning and/or conditioning environment, and most especially in automatic machines used for laundry and/or dish cleaning.

The present invention addresses and resolves all of the inadequacies and deficiencies associated with conventional monitoring devices by providing a self-contained, wireless sensor device, preferably the sensor device is free-floating and/or neutrally buoyant within the environment which allows the surrounding environment within which the sensor device is present to freely contact the sensor element ("sensor") of the sensor device.

The present invention resolves all of the problems associated with conventional monitoring devices, particularly with regards to versatility. Indeed, the sensor device may be adapted to sense a chemical and/or physical characteristic in an environment of any chemical phase including gas, liquid, solid and combinations thereof. Indeed, the sensor device may be adapted to measure and record in a high-shock environment.

In one aspect of the present invention, a self-contained, wireless sensor device comprising a sensor element capable of continuously detecting, identifying and/or measuring a chemical and/or physical characteristic of a surrounding environment, such as a liquid medium, static or dynamic, as the surrounding environment freely contacts the sensor elements of the sensor device during the time period the sensor element is activated within the surrounding environment, is provided. A sensor element is activated when it is in its measuring and/or detecting and/or identifying operating mode. In one embodiment, the sensor element(s) are continuously monitoring a surrounding environment even though the sensor device does not start recording the characteristics measured and/or detected and/or identified until such time that the sensor element(s) measure and/or detect and/or identify a predetermined condition in the surrounding environment. In another embodiment, the sensor element is activated manually so that any and/or all characteristics measured and/or detected and/or identified by the sensor element are recorded by the recording component of the sensor device.

In another aspect of the present invention, a self-contained, wireless sensor device comprising:
  a. a sensor element capable of continuously detecting, identifying and/or measuring a chemical and/or physical characteristic of a surrounding environment, such as a liquid medium, as the surrounding environment freely contacts the sensor element during the time period the sensor element is activated within the surrounding environment;
  b. a data storage component, wherein the data storage component is in communication with the sensor element such that the chemical and/or physical characteristic detected, identified and/or measured by the sensor element is retrievably stored in the data storage component;
  c. a stored data exchanger component capable of retrieving the stored chemical and/or physical characteristic from the data storage component and forwarding the characteristic to an external data collector;
  d. a power source; and
  e. a housing that houses components a.–d, is provided.

In still another aspect of the present invention, a method for detecting, identifying and/or measuring a chemical and/or physical characteristic of a surrounding environment, such as a liquid medium, comprising:
  a. providing a sensor device according to the present invention;
  b. placing the sensor device in the surrounding environment; and
  c. activating the sensor element of the sensor device such that the sensor detects, identifies and/or measures the chemical and/or physical characteristic of the surrounding environment; and
  d. optionally, storing the detected and/or identified and/or measuring the chemical and/or physical characteristic; and
  e. optionally, communicating the stored characteristic to an external data collector, preferably via a conductive link and/or inductive link and/or radio frequency, is provided.

In even yet another aspect of the present invention, a method for formulating a product, wherein the method comprises:
  a. providing a sensor device according to the present invention;
  b. placing the sensor device in a surrounding environment, such as a liquid medium, such that sensor of the sensor device detects, identifies and/or measures a chemical and/or physical characteristic of the surrounding environment during the time period the sensor is activated; and
  c. considering the detected, identified and/or measured chemical and/or physical characteristic to formulate the product, is provided.

In still yet another aspect of the present invention, a method for identifying a desired result in a liquid medium, wherein the method comprises:
  a. providing a sensor device according to the present invention;
  b. placing the sensor device in a surrounding environment, such as a liquid medium, such that sensor of the sensor device detects, identifies and/or measures a chemical and/or physical characteristic of the surrounding environment during the time period the sensor is activated; and
  c. considering the detected, identified and/or measured chemical and/or physical characteristic to determine any action that is needed to be taken upon the surrounding environment to achieve the desired result; and
  d. optionally, taking the action determined in c), is provided.

In still another aspect of the present invention, an article of manufacture comprising:
  a. a sensor device according to the present invention; and
  b. instructions for using the sensor device for detecting, identifying and/or measuring a chemical and/or physical characteristic of a surrounding environment, is provided.

In but another aspect of the present invention, a method of monitoring an environment, comprising the steps of:
  a. remitting a sensor device in accordance with the present invention to a surrounding environment for which monitoring is sought;
  b. activating the sensor device such that the sensor elements of the sensor device measure and/or detect and/or identify a chemical and/or physical characteristic of the surrounding environment;
  c. recovering the sensor device, preferably following a predetermined time period and/or predetermined number of placements of the device into said environment; and
  d. examining the recorded characteristic values of the surrounding environment; and
  e. optionally, making a business and/or commercial and/or technical and/or marketing decision based upon the examination, is provided.

In yet another aspect, there are provided methods of doing research, especially consumer research, into washing of laundry in automatic laundry machines and/or operating automatic laundry machines utilizing the above described device.

In other aspects of the invention there are provided similar devices and methods of doing research in automatic dishwashing machines and/or operating automatic dishwashing machines.

In one embodiment, the device may be a fully integrated, multi-sensor element sensor device that encompasses all of the aforementioned features, while being adapted for tremendously simple operation.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

All documents cited in the Detailed Description of the Invention are, in relevant part, incorporated herein by reference; the citation of any document is not to be construed as an admission that it is prior art with respect to the present invention.

DETAILED DESCRIPTION OF THE INVENTION

Definitions

Figure 1:
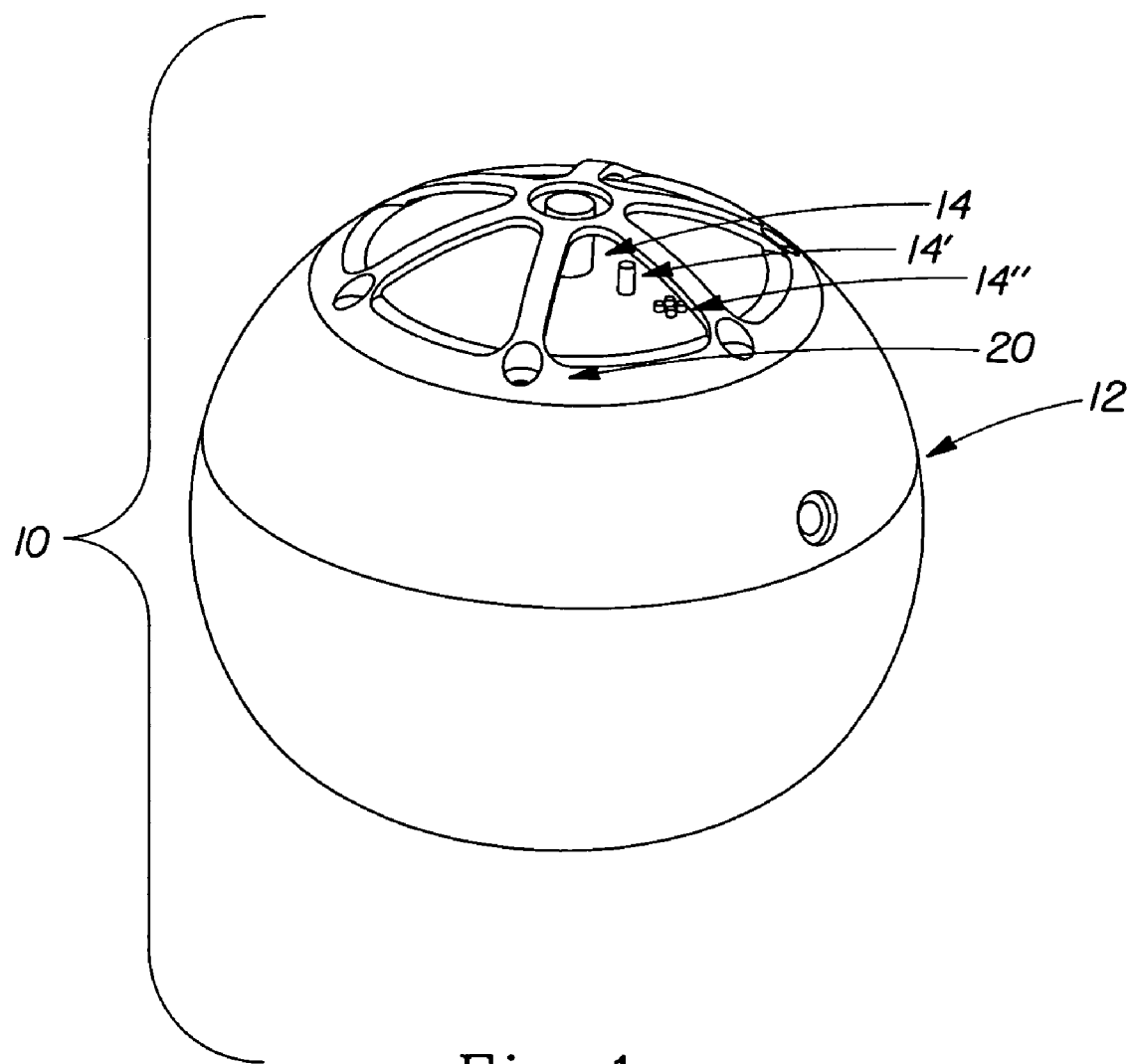
FIG. 1 represents a perspective view of one of the preferred aspects of the monitoring and recording device of the first embodiment.

As used herein, "self-contained, wireless" means that for its operation, the sensor device needs no physical connection with an external source, such as an energy source, processing unit or the like. As a result of the sensor device being self-contained and wireless, the sensor device can be freely positioned in a surrounding environment, such as a liquid medium. Further, the positioning of the sensor device of the present invention can change during its presence in the surrounding environment.

As used herein, "chemical and/or physical characteristic" (alternatively "chemical and/or physical parameter") means a condition and/or ingredient and/or property of the surrounding environment. Nonlimiting examples of such characteristics include pH, conductivity, temperature, turbidity, ingredient concentrations, infrared properties, presence of metal oxides, water hardness, viscosity, presence of minerals, TOC, BOD, presence of halogens (such as chlorine), pressure, biological activity, UV/VIS absorption properties, ion content, presence of bleach, presence of oxygen, radiation properties, strain, agitation, acceleration, especially 3-axis acceleration, vibration, velocity and/or density. Such characteristics are capable of being sensed, for example, by pH sensors, conductivity sensors, temperature sensors, turbidity sensors, liquid medium ingredient concentrations, infrared sensors, metal oxide sensors, water hardness sensors, viscosity sensors, mineral sensors, TOC sensors, BOD sensors, chlorine sensors, pressure sensors, biological activity sensors, UV/VIS absorption sensors, ion content sensors, bleach sensors, oxygen sensors, refractive index sensors, surface plasmon resonance (SPR) sensors, quartz crystal microbalance (QCM) sensors, conductive polymer sensors, available chlorines (AvCl) sensors, available oxygen (AvO) sensors, relative humidity sensors, oxidation-reduction potential (ORP) sensors, radiation sensors, density sensors and mixtures thereof.

"Sensor element" and/or "sensor" as used herein is a device that is capable of detecting, identifying and/or measuring a certain characteristic of a surrounding environment within which the sensor device is present. In one embodiment, the sensor comprises a chip and/or other electronic devices that measures and/or detects and/or identifies a characteristic existing and/or being present in the sensor element's surrounding environment. Those of ordinary skill in the art can select the proper sensor(s) to be part of the sensor device based upon the characteristics desired to be detected, identified and/or measured, and/or based on the surrounding environment within which the sensor device will be operated.

"Surrounding environment" as used herein means an environment comprised of organic and/or inorganic, living and/or nonliving, solids, liquids, gases, inanimate, animate, materials.

"Liquid medium" as used herein means any liquid environment contained within an article of manufacture or present in nature including, but not limited to, bodies of water, rivers, swimming pools, streams, wash liquor, sump pumps, wells, water lines, sewers, hot tubs, oil wells, process mixers, water treatment plants, desalinization processing equipment, streams, sewage treatment plants, water softeners, rain water, effluent, oceans, wash liquors, water recycling plant, nuclear reactors, wine processing equipment, beer brewing equipment, and the like.

"Data storage component" as used herein means an article, such as a computer chip or circuit board or PC board, capable of receiving and storing the measured and/or detected and/or identified characteristic information from a sensor component.

"Power source" as used herein means a power source capable of storing energy (power), such as a battery or a solar power source, and any components associated with forming the power source.

Sensor Device

Figure 2:
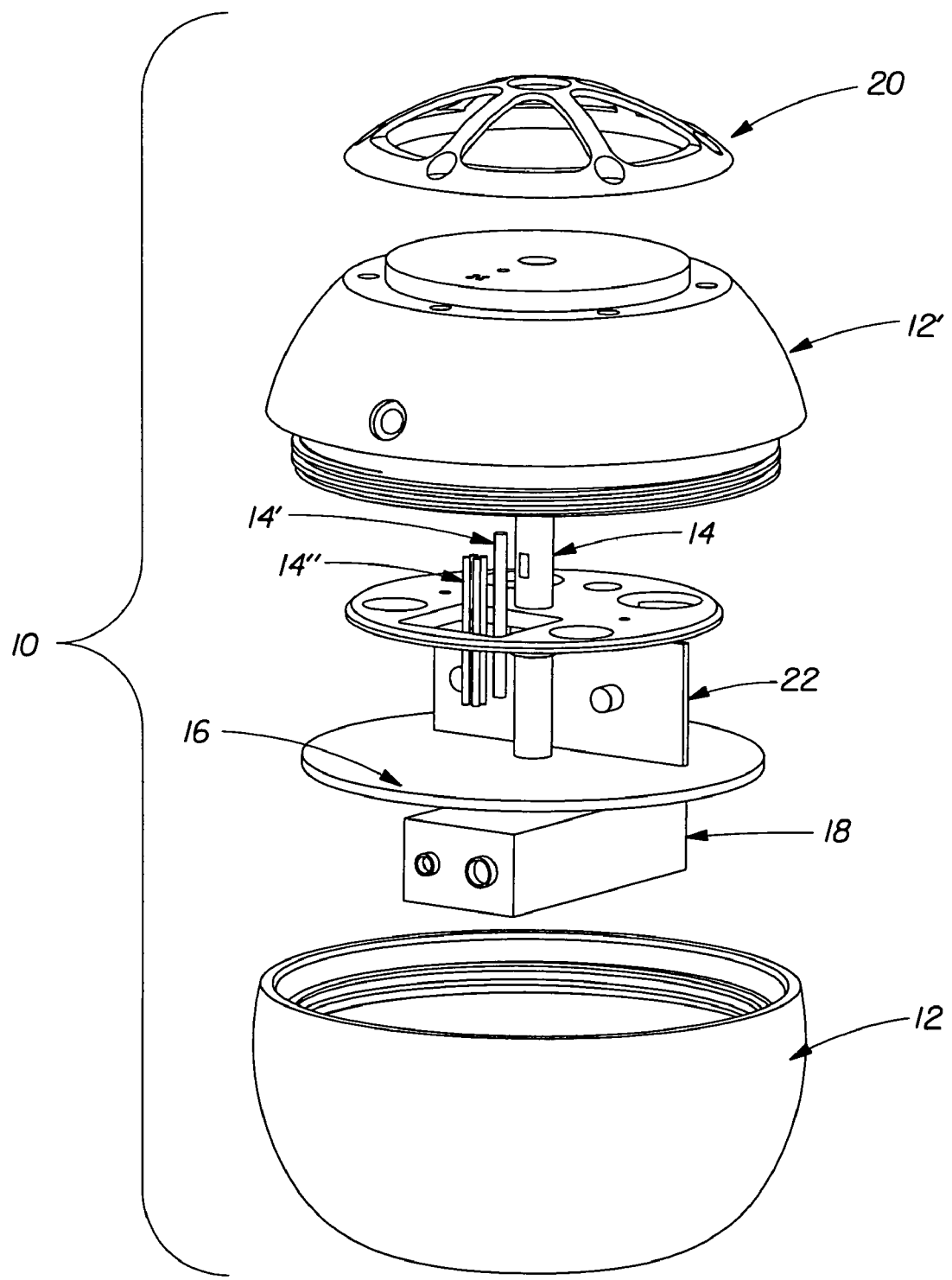
FIG. 2 represents an expanded view of the device depicted in FIG. 1.
Figure 3:
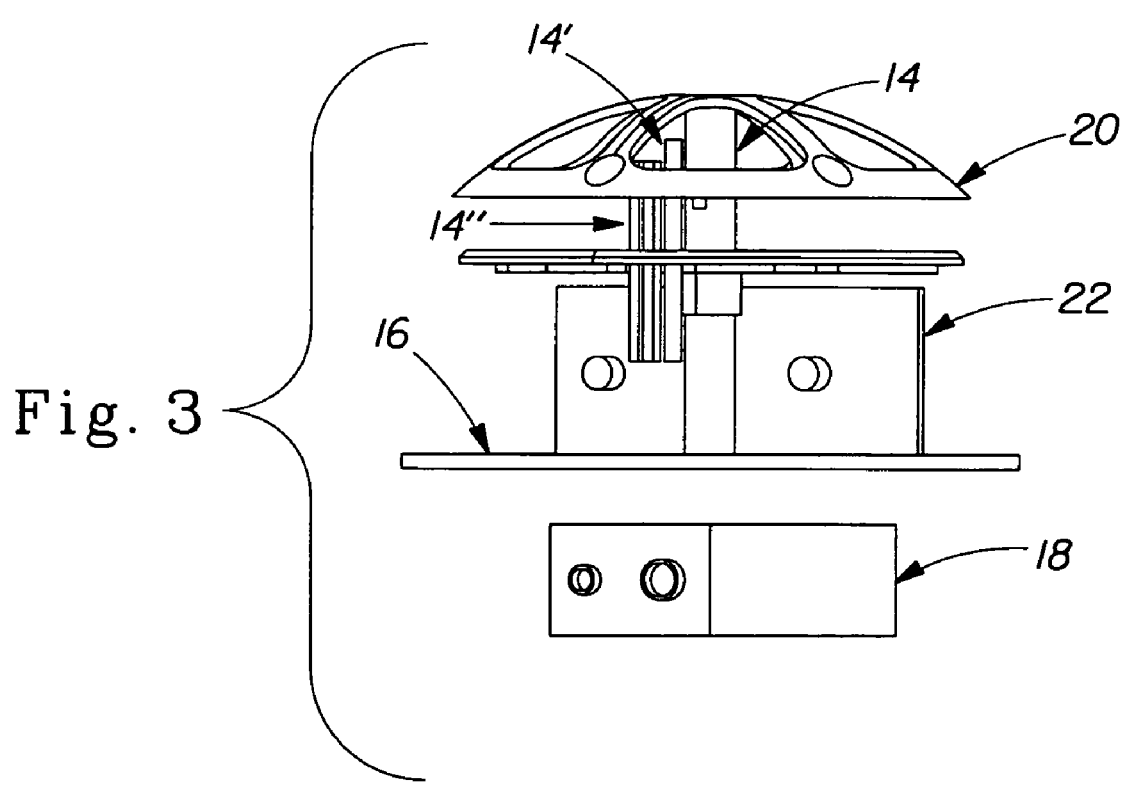
FIG. 3 represents a perspective view of a portion of the device depicted in FIG. 2.

As shown in FIGS. 1 and 2, a sensor device 10 in accordance with the present invention, comprises a housing 12. The housing 12 can be in the form of any shape. Nonlimiting examples include conical shapes, cylinder shapes, cube shapes, globular shapes and spherical shapes. Without wishing to be bound by theory, it is believed that a spherically shaped housing component minimizes encumbrances encountered by the sensor device upon deployment in the environment for which monitoring is sought. For the consumer useful environment, such as in a clothes washer or a dishwasher, the housing preferably has a generally globular shape, such as oval, more preferably a generally spherical shape, to minimize the entanglement with the objects to be cleaned.

The housing 12 can have various sizes depending on applications. In one preferred embodiment, for a consumer useful environment, such as in a clothes washer or a dishwasher, it is preferable that the sensor device of the present invention be compact and portable. In this embodiment, the housing of the sensor device typically has a dimension of less than about 40 cm, preferably less than about 30 cm, and more preferably less than about 20 cm. However, it is preferable that the sensor device is not too small so it can be located and recovered easily and conveniently, thus, typically the sensor of the present invention has a size of at least about 2 cm, preferably at least about 5 cm, and more preferably at least about 8 cm. It is desirable that the housing of the sensor device is such that entanglement with other items within the environment in which the sensor device is deployed is mitigated.

A spherical shaped housing is shown in FIGS. 1 and 2. The housing 12 may be a one-piece structure, but preferably it is a two or more-piece structure such that the internal components can be accessed and/or replaced from time to time. If the housing 12 is a two or more-piece structure then the housing 12 preferably incorporates removable and/or replaceable attaching elements, such as screws, and any necessary and appropriate seals, such as O-rings, to hold the housing 12 together when in its operational state. This is especially true for tailoring the sensor device 10 for different surrounding environments and different characteristics to be measured and/or detected and/or identified.

The housing 12 is preferably designed to protect the internal components from damage. The housing 12 preferably comprises a chemical and/or physical and/or solvent and/or impact resistant material. The housing 12 is preferably designed to absorb impact forces of greater than 50 g. The housing 12 can be made by any suitable process known by those skilled in the art. For example the housing 12 can be made by an injection molding process.

The housing 12 preferably is sized such that the sensor device 10 can be carried and handled by an operator in one hand, e.g., the size of a baseball and/or softball. The sensor device 10 preferably is of a size and shape that avoids being encumbered in any particular surrounding environment.

In addition to the housing 12, the sensor device 10 of the present invention comprises a sensor component comprising one or more sensor elements 14, 14' and 14", for example, a data storage component 16, a power source 18 as shown in FIG. 2, and preferably a protective element 20 to protect the sensor elements. The sensor component comprises one or more sensor elements such as a pH sensor element 14, a conductive sensor element 14' and a temperature sensor element 14". The sensor elements 14, 14' and 14" can be designed to sense (i.e., measure and/or detect and/or identify) various characteristics, especially chemical and/or physical characteristics, existing or being present in a surrounding environment of the sensor elements. Each sensor element shall be adapted to the characteristic to be measured and/or detected and/or identified, and the choice of the appropriate sensor element will be easily determined by a person skilled in the art. Sometimes sensor elements can be adapted to sense more than one characteristic.

One type of sensor element for use in the sensor device 10 of the present invention is a conductivity sensor element 14'. A conductivity sensor element 14' can be achieved for example by a two-contact or a four-contact (as shown) capacitive measurement device. The contacts may be coated with a thin layer of non-conductive protective material thereby mitigating the risk of contact degradation through electrochemical action. It should be noted that any measurement of ionic conductivity, such as this, should be preferably performed using alternating signals (alternating current) to prevent ion migration opposing an applied direct current field. The measurement with such a four contact sensor is done by passing an ac current, which is measured (A), through the liquid via the two outer contacts, and measuring the voltage (V) developed across the two inner contacts. The conductivity of the liquid is proportional to A/V, irrespective of the contamination between the contacts and the liquid (such a contamination is usually due to accumulation of compounds on the surface of the electrodes).

The sensor device 10 of the present invention may comprise both a conductivity sensor element 14' and a pH sensor element 14 in close proximity, for example less than 4 and/or 2 and/or 1.5 inches of separation, to one another within the sensor device, preferably adjacent to one another. This feature of the device presents particular novelty, as conventional monitoring devices are not adapted for placement of the subject sensors in close proximity to each other. No other monitoring device is adapted to facilitate the coordinated transmission of signals produced by sensors, so as to prevent interference between the said signals.

The sensor component preferably comprises more than one sensor element such that more than one sensor element multiplex. In other words, two or more or three or more or four or more sensor elements are measuring and/or detecting and/or identifying a physical and/or chemical characteristic simultaneously or almost simultaneously.

The housing 12 is designed such that the sensor elements of the sensor component are in communication, especially fluid communication in a liquid medium, with the characteristic to be measured and/or detected and/or identified by each respective sensor element. In other words, the environment is in functional contact with the sensors elements.

The data storage component 16 may comprise one or more data storage elements 22 such as PC boards, logger boards, circuit boards, computer chips, which are in communication, preferably via electronics, with the sensor elements of the sensor component such that sensed (i.e., measured and/or detected and/or identified) characteristic information is retrievably stored in the data storage component 16. The storage of such information may be extremely short such as one-tenth of a second or a second such as in the case of information being temporarily stored in the data storage component 16 before being transmitted to an external receiving component via electronic means and/or radio frequency means, in other words, the sensor device 10 may comprise a telemetry system. Alternatively, the storage of such information may be relatively longer, such as the period of time for a wash cycle in a washing machine to be completed.

The data storage component 16 may comprise one or more data storage elements 22 such that preferably about 20, more preferably about 50, most preferably about 100 or more characteristics/second/hour of characteristic information is stored on said one or more data storage elements 22.

The data storage component 16 preferably comprises an outlet (not shown) through which the stored data can be downloaded to a computer or other electronic information-processing device after the sensor device 10 has been removed from the environment. The computer and/or information-processing device will convert the characteristic value into a human recognizable value.

The power source 18 can be a battery, disposable or rechargeable, and/or solar power device.

The sensor device of the present invention can be turned on and off either manually or by a sensor element sensing a characteristic in the sensor device's surrounding environment at any time during the sensor device's presence within the surrounding environment. For example, the sensor component may be activated by a chemical and/or physical characteristic acting on one or more sensor elements of the sensor device.

The sensor device of the present invention may be a "smart" alternative to conventional "dumb" monitoring devices. By "smart" it is meant that the device can be automatically turned on and off due to the presence of a characteristic of the environment/liquid media and/or that the device can measure and/or detect and/or identify various physical and/or chemical characteristics of the environment without having to have been programmed, prior to deployment, for specific characteristics. By "dumb" is meant that the device has to be turned on manually and that the device has to be programmed to measure and/or detect and/or identify a specific characteristic.

The sensor device of the present invention may be designed such that when it is placed in a liquid medium, such as a body of water, such as a river, it can adapt to its surrounding environment by repositioning itself to ensure that the sensor elements of the sensor device are underwater. The sensor device can further comprise a means of adjusting the buoyancy of the device, such that the device conducts measurements at any level of a liquid medium, including the top, middle and/or bottom of the environment for which monitoring is sought. No other conventional monitoring device is adapted for the adjustment of the buoyancy of the device by the practitioner, to customize the device for placement at varying levels in a liquid environment in which the device is deployed. The sensor device can be designed to have a neutral density, lesser density or greater density of the liquid medium to tailor where in the liquid media the sensor device and hence the sensor elements will be positioned. This is especially useful if the liquid medium comprises two or more phases.

Depending on the application and the parameter(s) for which monitoring is sought, the sensor device may be weighted, to facilitate the adjustment of its buoyancy. In another preferred aspect of the present embodiment, the sensor device may be weighted to facilitate contact between the sensor elements of the device and the environment for which monitoring is sought, particularly when said environment is entirely liquid. In yet another aspect of the present embodiment, the releasably associated halves of the housing component aid in the adjustment of the buoyancy of the sensor device by facilitating internal weighting of the device.

In yet another preferred aspect of the present embodiment, the sensor device will possess a neutral density, lower density or greater density, in comparison to the environment in which the device is deployed. The controlled density characteristic of the claimed device enables those who practice the present invention to predict and facilitate the placement of the sensor device at any level, in any environment. The controlled density feature of the sensor device is particularly useful when deployment of the device into a multi-phase environment is desired.

The sensor device of the present invention can be used to provide in vitro testing of surrounding environments, such as a liquid medium. The sensor device is preferably liquid tight such that the liquid medium is prevented from coming into contact with the data storage component and/or power source.

The sensor device of the present invention can be used to provide real-time analysis of surrounding environments, such as liquid media. "Real time" analysis is possible due to the fact that the surrounding environment can freely contact one or more sensor elements of the sensor device, rather than the sensor device collecting "snap-shot" aliquots of the surrounding environment.

The sensor device of the present invention is very versatile and can be used to measure and/or detect and/or identify characteristics of a surrounding environment, whether that environment is for example a liquid media, air, gas, or a biological media. The sensor device of the present invention can be used for analytical purposes, such as environmental sites, hazardous waste sites, oil wells, closed vessel environments, washing liquors, recreational purposes, medicinal purposes, physiological purposes, temporal purposes such as triggering some action upon a characteristic being sensed by, a sensor element of the sensor device.

The sensor device of the present invention may optionally comprise a dosing compartment for retaining a volume of material to be released from the sensor device upon a characteristic being sensed by a sensor element.

Even though specific sensor elements have been discussed with respect to the sensor devices as shown in the drawings, the present invention is not limited to a certain number of sensor elements being present in the sensor device, nor is it limited to the types of sensor elements being present in the sensor device.

The sensor device can be adapted to record the time and date on which a chemical and/or physical characteristic is measured. It also can be adapted to transmit real time measurement data, such that those who wish to deploy the device may readily ascertain the properties of the surrounding environment in which it is deployed, during its deployment. Further, it can be adapted to record characteristic values for subsequent retrieval. Still further, it can be adapted to transmit the recorded characteristic values via wire or wireless transmission. Still further yet, it can be adapted to transmit recorded characteristic values to a remote location, depending on the needs of those who utilize the sensor device.

The Housing Component

In a preferred aspect of the present embodiment, the housing component is designed to protect the internal components of the sensor device. Thus, the housing component preferably comprises a material that is adapted to sustain the physical and/or chemical elements present in the environment in which deployment of the sensor device is intended. Indeed, great impact forces characterize typical fabric and dish cleaning and/or conditioning environments. Moreover, high pressure may characterize the deep, natural and artificial water environments, which the sensor device is adapted to monitor. Thus, in a preferred aspect of the present embodiment, the housing component of the claimed device comprises an impact-resistant material, adapted to withstand impact forces of greater than 50 g and/or greater than 100 g.

Examples of suitable materials, especially plastics, metals, thermopolymers, thermosets and rubber, for constructing the housing component of the claimed invention, include, but are not limited to: polypropylene, polyethylene, polystyrene, polycarbonate, stainless steel, natural rubber, styrene-butadiene rubber, polybutadiene rubber, ethylene/propylene rubber, butyl- and chloro-butyl rubber, polyisoprene, nitrile and polyacrylate rubbers, Neoprene® and Hypalon®, silicone rubber, fluorocarbon rubbers, urethane elastomers, Lexan® and/or latex or foam rubber.

The housing component of the present embodiment may be made following known processes in the art. For example, the housing component may be made by an injection molding process.

In another preferred aspect of the present embodiment, the housing component is designed such that it facilitates contact, preferably free contact, between the sensor element of the sensor component and the environment in which the device is deployed. That is to say, the housing component of the present embodiment is designed to protect those constituents of the sensor device that are not adapted for exposure to the subject environment, while facilitating the introduction to the environment of those constituents that are intended for such exposure. In accordance with this, preferred aspect of the present housing component, one or more of the sensor elements of the sensor component is/are contained within the housing component.

In another preferred aspect of the present embodiment, the housing component comprises a protective element. Preferably, the protective element protects those constituents of the sensor device that are adapted for exposure to the subject surrounding environment, such as the external sensor elements of the sensor component. The protective element may also be employed to protect the LED or manual controls of the sensor device, depending on the application and/or environment for which deployment of the device is sought.

The Sensor Component

Commercially available sensor elements suitable for the sensor component of the present embodiment may be obtained from several suppliers, including, but not limited to: Orion, Honeywell, Rosemont, Microsensors Inc., TBI-Bailey, Foxboro, Sentron, WTI Inc., Hanna Instruments, Sensor-Tech, Lazar Labs, Onset Computer Corp and Gemini.

In one aspect of the present embodiment, the sensor component of the sensor device comprises two sensor elements, preferably adapted to sense agitation and temperature, in close proximity to each other. In yet another embodiment, the sensor component of the sensor device measures the value of one or more of the aforementioned chemical and/or physical parameters directly and determines the value of other such parameters indirectly. By "indirectly", it is meant that the sensor device is adapted to determine the value of chemical and/or physical parameters of the environment in which it is employed without directly sensing said parameters. Without wishing to be bound by theory, the indirect sensing feature of the present embodiment is achieved via internal processing of directly sensed parameters and application of conversion and/or extrapolation formulas.

In another aspect of the present invention, especially when the sensor device is adapted to sense and record the parameters of pH and/or conductivity, the sensor device can be adapted to sense and record the characteristic of temperature. In a highly preferred aspect of the present invention, the sensor device comprises four sensor elements. In yet another highly preferred aspect of the present invention, the sensor device comprises four sensor elements, one adapted to sense temperature, one adapted to sense conductivity, one adapted to sense pH and one adapted to sense acceleration. Fewer than four sensor elements could be used if one or more sensor elements could sense two or more of the characteristics.

Multiplexing as, discussed in more detail in "The Recording Component" section herein below, facilitates the placement and operation of sensor elements in close proximity, for example adjacent to one another. That is to say, the sensor device is adapted to sense and record the value of one or more chemical and/or physical parameters upon placement of the sensors in close proximity to each other, on the claimed device. No other device is adapted to convey this benefit, as the placement of sensors in close proximity typically generates signal interference between said sensors. Without wishing to be bound by theory, it is believed that the multiplexing coordinates the signals of the present sensor elements, such that the sensors do not transmit signals simultaneously, and thus, do not interfere with each other.

In a preferred aspect of the present embodiment, the sensor component of the sensor device transmits an analog output signal to an analog-to-digital converter (A/D) of the sensor device. In another aspect of the present embodiment, the A/D converter can either be part of a microcontroller unit or a unit separate from the microcontroller. Preferably, the A/D converter of the sensor device converts the analog signals received from the sensor component(s) to a digital signal that can be used by the microcontroller. Preferably, the microcontroller can either store the digital signal directly to memory or perform math on the incoming signals before storing to memory. In another preferred aspect of the present invention, specific circuitry (or a digital transducer) is employed to achieve transmission of the signal from the sensor component of the sensor device.

The Recording Component

The recording component of the present embodiment of the claimed invention is further adapted to record, upon sensing, the value of one or more parameters measured by the sensor component. The recording component, or data collection means, of the present embodiment preferably comprises the following constituents: a memory means, a microcontroller, an analog-to-digital converter means and a digital input and/or output. In a preferred aspect of the present embodiment, the sensor device comprises a memory means that is employed to store the information collected by the sensor component of the present embodiment for later access by the microcontroller of the present embodiment. In another preferred aspect of the present embodiment, the memory means is employed to store the software and/or variables with which the microcontroller is controlled.

In another preferred aspect of the present embodiment, both volatile and non-volatile portions characterize the memory means of the present invention. Preferably, the information collected by the sensor component of the present embodiment is stored in non-volatile memory. In a preferred aspect of the present embodiment, the sensor component memory means comprises at least about 32 kilobytes of space, more preferably at least about 64 kilobytes. In yet another preferred aspect of the present embodiment, the microcontroller uses non-volatile ROM memory means to execute a previously stored program. Also, the microcontroller uses a volatile memory to store temporary variables during program execution.

The recording component of the present invention preferably further comprises a microcontroller. In a preferred aspect of the present invention, the microcontroller stores data to and reads data from the memory means of the present embodiment. Preferably, the microcontroller of the present embodiment comprises a means with which the device may conduct microsecond time measurement. Without wishing to be bound by theory, the timer of the microcontroller is employed to measure the duration of the signal or value sensed by the sensor component of the present embodiment. In a preferred aspect of the present embodiment, the microcontroller will further comprise timer/counter unit. When present, the timer/counter unit enables the microcontroller to index the data sensed by the sensor component of the present embodiment as a function of the time and date when which the microcontroller receives the sensed signal. That is to say, the timer/counter unit of the present embodiment controls and documents the frequency with which a chemical and/or physical characteristic is sensed and/or recorded. Of course, practitioners of the sensor device will know the time at which the device is employed in the environment for which measurement is sought. By using the timer/counter unit of the present embodiment, practitioners may further determine the exact time at which a particular chemical and/or physical characteristic was measured. Without wishing to be bound by theory, this may be achieved by correlating the time of deployment of the sensor device into the subject environment with the frequency of measurement set by the timer/counter unit of the sensor device.

Whether idle or active, another aspect of the present recording means facilitates the light emitting diode (LED) of the sensor device's operational status. Preferably, the LED of the present embodiment will facilitate the display of at least two functions: active data-acquisition mode and standby mode. In a highly preferred aspect of the present embodiment, the LED indicates the status of the device, whether in active data-acquisition mode or standby mode, via a constant or flashing single-colored light. For example, the constant illumination of a red light via the display means indicates that the sensor device is in standby mode. Conversely, the flashing of said red light via the display means indicates that the sensor device is in active data-acquisition mode. In a less-preferred aspect of the present embodiment, the LED indicates the operational status of the device via the employment of a distinctive color for each operational status. For example, a green light may be illuminated on the LED when the device is in active data-acquisition mode. Conversely, a red light may be illuminated when the device is in standby mode.

In another aspect of the present embodiment, the sensor device, upon activation, continues to acquire data from the sensor component until a predetermined time period has elapsed. In yet another aspect of the present embodiment, the sensor device, upon activation, continues to collect data from the sensor component until such data reaches a predetermined value, at which time the sensor device enters standby mode.

In a preferred aspect of the present embodiment, the sensor component transmits data, in digital form, to the digital input/output means of the recording component. When transferred in digital form, the data sensed by the sensor component of the present invention may be transferred to a computer or similar device only to effectuate meaningful presentation of the data. For example, said data may be transferred to a computer for presentation in Microsoft® Excel. Otherwise, said data possesses a form that is suitable for immediate interpretation by the practitioner of the sensor device. In yet another preferred aspect of the present embodiment, the sensor component transmits data, in raw form, to the digital input/output means of the recording component. When transferred in raw form, the data sensed by the sensor component of the present invention may be digitized upon downloading the data to a computer or similar processing device. There exists a plethora of commercially available computers and/or processing devices that may be employed to digitize the raw data sensed by the sensor component of the present invention.

In another preferred aspect of the present embodiment, the recording component of the sensor device comprises an interface assembly. Preferably, the interface assembly transmits the sensed values from the sensor component to the recording component. Preferably, the interface assembly comprises a multiplexing means, a voltage protection means and a high-resolution analog-to-digital means. In a preferred aspect of the present embodiment, the interface assembly is situated on the circuit board of the sensor device.

In yet another preferred aspect of the present embodiment, the multiplexing means of the interface assembly is employed to transmit sensed values from the sensor component to the microcontroller of the recording component. Without wishing to be bound by theory, this transmission is achieved without transfer of the sensed signals through the multiplexing means. Rather, the microcontroller of the present embodiment receives the sensed values via the digital input/output means of the recording component. Preferably, the multiplexing means may be selected from any multiplexing means, suitable for employment in the sensor device and commercially available.

In another aspect of the present embodiment, the interface assembly of the recording component comprises a voltage protection means. Preferably, the voltage protection means of the present embodiment is connected to the high resolution analog-to-digital converter means and the multiplexing means of the recording component. Preferably, the voltage protection means serves the fundamental purpose of ensuring that the signal sensed by the sensor device does not exceed a certain strength, such that the signal does not exceed the electrical capacity of each component of the sensor device. Any suitable circuitry may be employed for the voltage protection means, depending upon the signal strength desired. Indeed, the electrical capacity of each component of the sensor device, and specifically the microcontroller, must be examined in selecting the appropriate signal strength.

In another aspect of the present embodiment, the high-resolution analog-to-digital converter of the recording component converts the sensed signal transmitted to the voltage protection means from analog to digital form. Preferably, the high-resolution analog-to-digital converter of the present embodiment is characterized by a signal strength of about 12 bits, preferably 16 bits. The high-resolution analog-to-digital converter of the present embodiment serves the additional purpose of providing accurate, sensed chemical and/or physical data measurement, while facilitating the employment of simple circuitry for use in scaling. Preferably, the high resolution analog-to-digital conversion mechanism of the present embodiment transmits the sensed signal to the processing apparatus of the recording component.

In a preferred aspect of the present embodiment, the data collection rate of the recording component may be programmed to suit the needs of the practitioner. Preferably, the data collection rate of the recording component is relatively low, preferably as short as one-tenth of a second. A low data collection rate is particularly useful when temporary storage of data in the recording component is appropriate. In yet another preferred aspect of the present embodiment, the recording component of the sensor device comprises one or more storage elements. The number of chemical and/or physical parameters stored by the recording component of the present embodiment is entirely dependent on the type of processor employed in the sensor device. Indeed, there exist several, commercially available processors, each of which is designed to store a varying amount of data. The practitioner may select the appropriate processor for employment in the sensor device depending on the duration of the intended deployment(s) and the number of chemical and/or physical parameters for which measurement is sought. Preferably, the sensor device comprises a processor adapted to record all of the chemical and/or physical parameters associated with a single deployment, thereby eliminating the need to retrieve recorded data from the device before the completion of an intended deployment.

In a preferred aspect of the present embodiment, the data collection means of the recording component comprises an output or outlet mechanism to facilitate the transfer of stored data to an external data collector, such as a computer or similar processing device. Preferably, such data is transferred from the recording component of the sensor device to an external component via a number of means, including, but not limited to, electronic means, radio frequency means and/or infrared (IR) means. Thus, in another preferred aspect of the present embodiment, the sensor device is adapted to facilitate the wire or wireless transmission of stored data from the recording component to an external, processing component.

The Power Supply

The sensor device further comprises a power supply. Preferably, the power supply of the present embodiment is renewable and maybe selected from a battery and/or a solar power means. When a battery is selected for employment in the sensor device, such a battery may either be rechargeable or disposable in nature. Moreover, examples of a suitable battery of the present embodiment, whether rechargeable or disposable, include, but are not limited to: AA, AAA, C, D and 9-volt batteries. Other suitable batteries of the claimed invention, include, but are not limited to: lithium batteries, nickel batteries, cadmium batteries and kinetic batteries. Suitable batteries of the claimed invention are commercially available and sold under the trade names of Energizer®, Eveready®, Duracell®, Rayovac® and/or Panasonic®.

Method of Doing Business

In accordance with the second embodiment of the present invention, a method of doing business, comprising the steps of remitting the device of the first embodiment to an environment for which monitoring is sought, directing placement of the device into the said environment, recovering the device following a predetermined time period or predetermined number of placements of the device into said environment, and examining the recorded characteristic values of said environment, is disclosed.

When practiced in combination, the first and second embodiments of the claimed invention constitute a comprehensive method with which to monitor and record the environments under which fabric and dishes are cleaned and/or conditioned, as well as numerous other natural and artificial environments. Indeed, the recorded information obtained from practicing the claimed invention in accordance with the present embodiment may be used to adjust one or more characteristics of the environment in which the sensor device is deployed. As discussed below, the information obtained via practicing the present method is extremely useful for research and development, quality control and customer satisfaction of proprietary fabric and dish cleaning and/or conditioning products. Moreover, the information obtained via practicing the present invention is useful in adjusting one or more chemical and/or physical characteristics of the other environments in which the sensor device is deployed. Such adjustments to the environment may be manually completed by the user of the device or automatically by the device, such as by dosing some ingredient from the device and/or especially in the case of an environment within an appliance, by the device communicating an action needed to appliance.

In a preferred aspect of the present embodiment, the device of the previous embodiment is remitted to a domestic or commercial arena for placement in the environment for which monitoring is sought, preferably a fabric and dish cleaning and/or conditioning environment. Preferably, the microcontroller of the recording component of the previous embodiment is preprogrammed with variables, such that the signals sensed by the device may be scaled and recorded for subsequent interpretation. Thus, the claimed invention is equipped for immediate deployment into any environment of the practitioner's choosing. Non-limiting examples of such environments include a fabric or dish washing machine, a lake or stream, and/or a swimming pool.

The conventional method of doing consumer research in the laundry and dishwashing areas is to provide a panel of consumers with product and a means for recording their use of the product in their normal cleaning processes. Many significant decisions are made based upon this kind of research. It was determined by the use of sensors as described hereinafter that the recordation provided by the consumers was much less accurate than previously thought. Additionally, the amount of data and the depth of understanding made possible by the use of the sensors herein was much greater and infinitely more useful. Prior to the studies conducted during the evaluation of the sensors herein there was no appreciation of the inadequacy of the prior art methods or the quality of research that was possible.

In a practical method of doing consumer research, a specific sensor device as described more fully hereinafter, was provided to a panel of consumers who were also provided with paper sheets to record some of the data, which was recorded by the sensor device. The data resulting from the sensor device was compared to the data recorded by the consumers and the consumer recorded data was found to contain substantial errors, which would have resulted in significant errors in any work based upon the consumer, recorded data. The different data is summarized hereinafter.

The amount and accuracy of data provided by a sensor device in a consumer research project improves the results by more accurately reflecting what occurs, and with appropriate sensors, allows for much more data, since the sensors can record data, which the consumer and even trained research technicians could not obtain in real time.

The sensor device can also be used to control cleaning processes to make them more efficient. This is especially important in large scale commercial cleaning processes, where use of only enough materials to effect good cleaning provides more profits and less detergent ingredient to reclaim or dispose of. The sensor devices can also make sure that the rinse cycles are sufficient to eliminate unwanted residues, thus minimizing adverse effects on the subsequent user.

Upon selecting the arena to which remittance of the claimed device is sought, whether domestic or commercial, practitioners may determine the duration of the intended deployment. On this basis, practitioners may tailor the memory capacity, physical structure, and other characteristics of the claimed device, if they so desire. That is to say, if a lengthy deployment is intended, practitioners may wish to equip the claimed device with enhanced memory capacity. Likewise, if deployment in a peculiar or high-shock environment is sought, practitioners may customize the housing component, if necessary. Along these lines, practitioners may formulate a plan of deployment, outlining the number of intended deployments into the intended environment and the duration of each deployment.

In another aspect of the present embodiment, practitioners may activate the device of the previous embodiment either manually or automatically. Preferably, practitioners will activate the device automatically, via deployment of the device into the environment for which monitoring is desired. The sensor device may activate automatically upon the sensing of a predetermined value by the sensor component of the previous embodiment. As discussed above, the sensor elements of the sensor component can continuously monitor the value of corresponding parameters, until the value reaches a predetermined threshold—at which time the device, specifically the recording component activates. In other words, the sensor component directs the digitization of the subject data. The automatic sensing feature of the present embodiment facilitates the conservation of power and memory, such that the recording means only stores meaningful, sensed data. In doing so, the automatic sensing feature of the present invention maximizes the storage of meaningful data, particularly in comparison with conventional monitoring devices. In yet another preferred aspect of the claimed invention, the sensor device is manually stimulated to induce its activation. According to the method of the present embodiment, the device may remain in the environment in which it is deployed for a predetermined time period or until the sensed values no longer meet the threshold required for data-acquisition mode.

In another aspect of the present embodiment, the device is removed from the environment in which it is deployed upon the duration of the predetermined time period or deactivation of the device (indicated via the LED). Upon removal of the device from the environment, the practitioner may engage in the retrieval of the information recorded by the device. Such retrieval may be accomplished via connection to an external component, in accordance with the previous embodiment. Preferably, upon reviewing the recorded parameters of the environment, the practitioner may adjust a chemical and/or physical characteristic of said environment.

In yet another preferred aspect of the present embodiment, the practitioner may obtain the recorded characteristic values from the testing environment to which the device is remitted, subsequent to recovery of the device from the testing environment. That is to say, in the case of a consumer testing environment, the practitioner may retrieve the results of the deployment of the device before the consumer returns the device to the user. There are several ways in which to retrieve the information recorded by the device subsequent to recovery of the device from the environment in which it is deployed. Preferably, an individual in the environment to which the device is remitted may report the recorded parameters via the World Wide Web or telephone system. In using the World Wide Web, an individual may either remit the information via electronic mail or report the findings directly to a pre-established Internet web site.

Upon examining the information reported to a designated system, whether the World Wide Web and/or telephone, the user of the device may adjust a chemical and/or physical characteristic of the environment in which the device is deployed. In the case of a consumer of fabric and dish cleaning and/or conditioning products, the user of the claimed device may inform the consumer as the characteristics of the environment in which the consumer is cleaning and/or conditioning fabric and dishes. In yet another preferred aspect of the claimed invention, the consumer can receive such information or instruction upon reporting the information to a World Wide Web address or telephone system. The information obtained from the sensor device is particularly useful in advising a consumer on proper use of proprietary fabric and dish cleaning and/or conditioning products, particularly when that consumer is experiencing difficulty doing so. Thus, the user of the sensor device, in accordance with the present embodiment, may be a manufacturer of proprietary fabric and dish products. Said user may employ the present method to engage in quality control, research and development and customer satisfaction of proprietary products. The user of the sensor device may also be engaged in the monitoring of a non-proprietary environment, such as a lake, stream and/or swimming pool.

While particular embodiments of the present invention have been illustrated and described, it would be obvious to those of ordinary skill in the art that various other changes and modifications can be made without departing from the spirit and scope of the invention. It is therefore intended to cover in the appended claims all such changes and modifications that are within the scope of this invention.

What is claimed is:

1. A self-contained, wireless sensor device comprising a sensor component comprising a first sensor element capable of activating the sensor device upon sensing a chemical and/or physical characteristic of a surrounding environment, a second sensor element capable of continuously detecting, identifying and/or measuring a chemical and/or physical characteristic of the surrounding environment when the sensor device is activated within the surrounding environment.

2. The sensor device according to claim 1 wherein the sensor device further comprises a data storage component, wherein the data storage component is in communication with the sensor element such that the chemical and/or physical characteristic detected, identified and/or measured by the sensor element is retrievably stored in the data storage component.

3. The sensor device according to claim 2 wherein the sensor device further comprises a stored data exchanger component capable of retrieving the stored chemical and/or physical characteristic from the data storage component and forwarding the characteristic to an external data collector.

4. The sensor device according to claim 3 wherein the stored data exchanger component is capable of receiving data from an external data source to the sensor device.

5. The sensor device according to claim 1 wherein the sensor device further comprises a communication component capable of communicating the chemical and/or physical characteristic detected, identified and/or measured by the sensor to an external data collector.

6. The sensor device according to claim 5 wherein the communication component is capable of receiving data from a data source external to the sensor device.

7. The sensor device according to claim 1 wherein the sensor device comprises a housing that houses the sensor.

8. The sensor device according to claim 1 wherein the first or the second sensor element is selected from the group consisting of pH sensors, conductivity sensors, temperature sensors, turbidity sensors, liquid medium ingredient concentrations, IR sensors, metal oxide sensors, water hardness sensors, viscosity sensors, mineral sensors, TOC sensors, BOD sensors, chlorine sensors, pressure sensors, biological activity sensors, UV/VIS absorption sensors, ion content sensors, bleach sensors, oxygen sensors, radiation sensors, density sensors and mixtures thereof.

9. The sensor device according to claim 1 wherein the first or the second sensor element is selected from the group consisting of: acceleration sensors, velocity sensors, vibration sensors, agitation sensors, strain sensors and mixtures thereof.

10. The sensor device according to claim 1 wherein the sensor device comprises a power source selected from the group consisting of: a battery, solar power device and mixtures thereof.

11. The sensor device according to claim 1 wherein the surrounding environment comprises a liquid medium.

12. The sensor device according to claim 11 wherein the sensor device is density matched to the liquid medium.

13. A method for detecting, identifying and/or measuring a chemical and/or physical characteristic of a surrounding environment comprising:
   a. providing a sensor device according to claim 1;
   b. placing the sensor device in the surrounding environment; and
   c. activating the sensor device such that the sensor element detects, identifies and/or measures the chemical and/or physical characteristic of the surrounding environment.

14. A method for collecting a chemical and/or physical characteristic of a surrounding environment comprising:
   a. providing a sensor device according to claim 1;
   b. placing the sensor device in the surrounding environment;
   c. activating the sensor device thereby at least one sensor element detects, identifies and/or measures the chemical and/or physical characteristic of the surrounding environment; and
   d. storing the chemical and/or physical characteristic in the sensor device; and
   d. optionally, communicating the stored chemical and/or physical characteristic to an external data collector.

15. A method for formulating a product, wherein the method comprises:
   a. providing a sensor device according to claim 1;
   b. placing the sensor device in a surrounding environment, such that at least one sensor element of the sensor device detects, identifies and/or measures a chemical and/or physical characteristic of the surrounding environment when the sensor is activated; and
   c. considering the detected, identified and/or measured chemical and/or physical characteristic to formulate the product.

16. A method for identifying a desired result in a liquid medium, wherein the method comprises:
   a. providing a sensor device according to claim 1;
   b. placing the sensor device in a liquid medium, such that at least one sensor element of the sensor device detects, identifies and/or measures a chemical and/or physical characteristic of the liquid medium when the sensor is activated; and
   c. considering the detected, identified and/or measured chemical and/or physical characteristic to determine any action that is needed to be taken upon the liquid medium to achieve the desired result; and
   d. optionally, taking the action determined in c.

17. An article of manufacture comprising:
   a. a sensor device according to claim 1; and
   b. instructions for using the sensor device for detecting, identifying and/or measuring a chemical and/or physical characteristic of a surrounding environment.

18. A method of monitoring an environment, comprising the steps of:
   a. remitting a sensor device according to claim 1 to a surrounding environment for which monitoring is sought;
   b. activating the sensor device such that one or more sensor elements of the sensor device measure and/or detect and/or identify a chemical and/or physical characteristic of the surrounding environment;
   c. recovering the sensor device; and
   d. examining the recorded characteristic values of the surrounding environment; and
   e. optionally, making a business and/or commercial and/or technical and/or marketing decision based upon the examination.

19. A method for doing consumer research relating to cleaning processes in automatic washing machines for laundry and/or dishware, the method comprising:
   a. providing a sensor device according to claim 1;
   b. providing instructions to the consumer to place the sensor device into the consumer's automatic washing machine and to operate the automatic washing machine such that the sensor device measures and/or detects and/or identifies a chemical and/or physical characteristic during the operation of the automatic washing machine;
   c. recovering the sensor device from the automatic washing machine; and
   d. optionally, analyzing the chemical and/or physical characteristic acquired by the sensor device.

* * * * *